(12) United States Patent
Bradley

(10) Patent No.: US 9,907,612 B2
(45) Date of Patent: Mar. 6, 2018

(54) COOLED MEDICAL HANDPIECE

(75) Inventor: David M. Bradley, Redwood City, CA (US)

(73) Assignee: SOLTA MEDICAL, INC., Hayward, CA (US)

(*) Notice: Subject to any disclaimer, the term of this patent is extended or adjusted under 35 U.S.C. 154(b) by 1194 days.

(21) Appl. No.: 13/225,636

(22) Filed: Sep. 6, 2011

(65) Prior Publication Data
US 2013/0060309 A1 Mar. 7, 2013

(51) Int. Cl.
| | |
|---|---|
| *A61B 18/18* | (2006.01) |
| *A61N 5/06* | (2006.01) |
| *A61B 18/00* | (2006.01) |
| *A61N 5/00* | (2006.01) |

(52) U.S. Cl.
CPC ........... *A61B 18/18* (2013.01); *A61N 5/0616* (2013.01); *A61B 2018/00011* (2013.01); *A61N 2005/005* (2013.01); *A61N 2005/0644* (2013.01); *A61N 2005/0649* (2013.01); *A61N 2005/0654* (2013.01)

(58) Field of Classification Search
USPC .......................................... 607/96, 100–102
See application file for complete search history.

(56) References Cited

U.S. PATENT DOCUMENTS

| | | | |
|---|---|---|---|
| 6,711,767 B2 * | 3/2004 | Klamm | 5/423 |
| 6,813,289 B2 | 11/2004 | Gruzdev et al. | |
| 2005/0010249 A1 * | 1/2005 | Minamoto | A61N 5/0616 607/2 |
| 2005/0171581 A1 * | 8/2005 | Connors et al. | 607/88 |
| 2006/0184165 A1 * | 8/2006 | Webster et al. | 606/41 |
| 2006/0206103 A1 | 9/2006 | Altshuler et al. | |
| 2008/0269851 A1 * | 10/2008 | Deem | A61B 18/18 607/101 |
| 2009/0306607 A1 * | 12/2009 | Yasuhiro | A61F 7/007 604/291 |

* cited by examiner

*Primary Examiner* — Joseph Stoklosa
*Assistant Examiner* — Adam Avigan
(74) *Attorney, Agent, or Firm* — Thompson Hine LLP

(57) ABSTRACT

Apparatus and methods for treating tissue with electromagnetic radiation. A handpiece includes a housing and a baffle that divides an interior space of the housing into first and second channels. The housing further includes a first opening and a second opening coupled in fluid communication with the first opening by the first channel. The apparatus further includes a heat-generating element, such as a source of electromagnetic radiation, disposed at least partially in the first channel and an air-moving device coupled with the first channel. The air-moving device is configured to generate a forced flow of cooling air entering at the first opening and exhausted at the second opening. The cooling air receives heat transferred from the heat-generating element, which cools the heat-generating element, and the heated cooling air is exhausted from the second opening in a direction away from the tissue that is being treated with the electromagnetic radiation.

15 Claims, 3 Drawing Sheets

COOLED MEDICAL HANDPIECE

BACKGROUND

The invention relates generally to devices for treating tissue with electromagnetic radiation and, in particular, to medical handpieces that are cooled with a forced air flow during operation.

Electromagnetic radiation (EMR) has found use in a wide variety of cosmetic and medical applications, including uses in dermatology for treating skin conditions. For most dermatological applications, the EMR treatment is performed with a device that delivers the EMR to the tissue surface. Conventional EMR treatments are typically designed to deliver radiation to induce a particular chemical reaction within the targeted tissue, to deliver radiation to cause an increase in tissue temperature, to deliver radiation to damage the targeted tissue, to cause a change at the skin surface, or to modify matter on the skin surface.

It would therefore be desirable to provide a medical handpiece that improves upon conventional medical handpieces.

SUMMARY

In an embodiment of the invention, an apparatus is provided for treating tissue with electromagnetic radiation. The apparatus includes a handpiece with a housing and a baffle that divides an interior space of the housing into a first channel and a second channel. The housing further includes a first opening and a second opening coupled in fluid communication with the first opening by the first channel. The apparatus further includes a heat-generating element disposed at least partially in the first channel and an air-moving device coupled with the first channel. The air-moving device is configured to generate a forced flow of air entering at the first opening and exhausted at the second opening.

In another embodiment, a method includes directing electromagnetic radiation out of a handpiece to treat tissue, and causing a forced flow of cooling air to enter through a first opening into a first channel extending through the handpiece. The method further includes directing the forced flow of cooling air within the first channel to transfer heat from a heat-generating element to the forced flow of cooling air. After the heat transfer occurs, the forced flow of cooling air is exhausted from the first channel through a second opening.

BRIEF DESCRIPTION OF THE FIGURES

The accompanying drawings, which are incorporated in and constitute a part of this specification, illustrate embodiments of the invention and, together with a general description of the invention given above, and the detailed description given below, serve to explain the principles of the embodiments of the invention.

DETAILED DESCRIPTION

Figure 1:
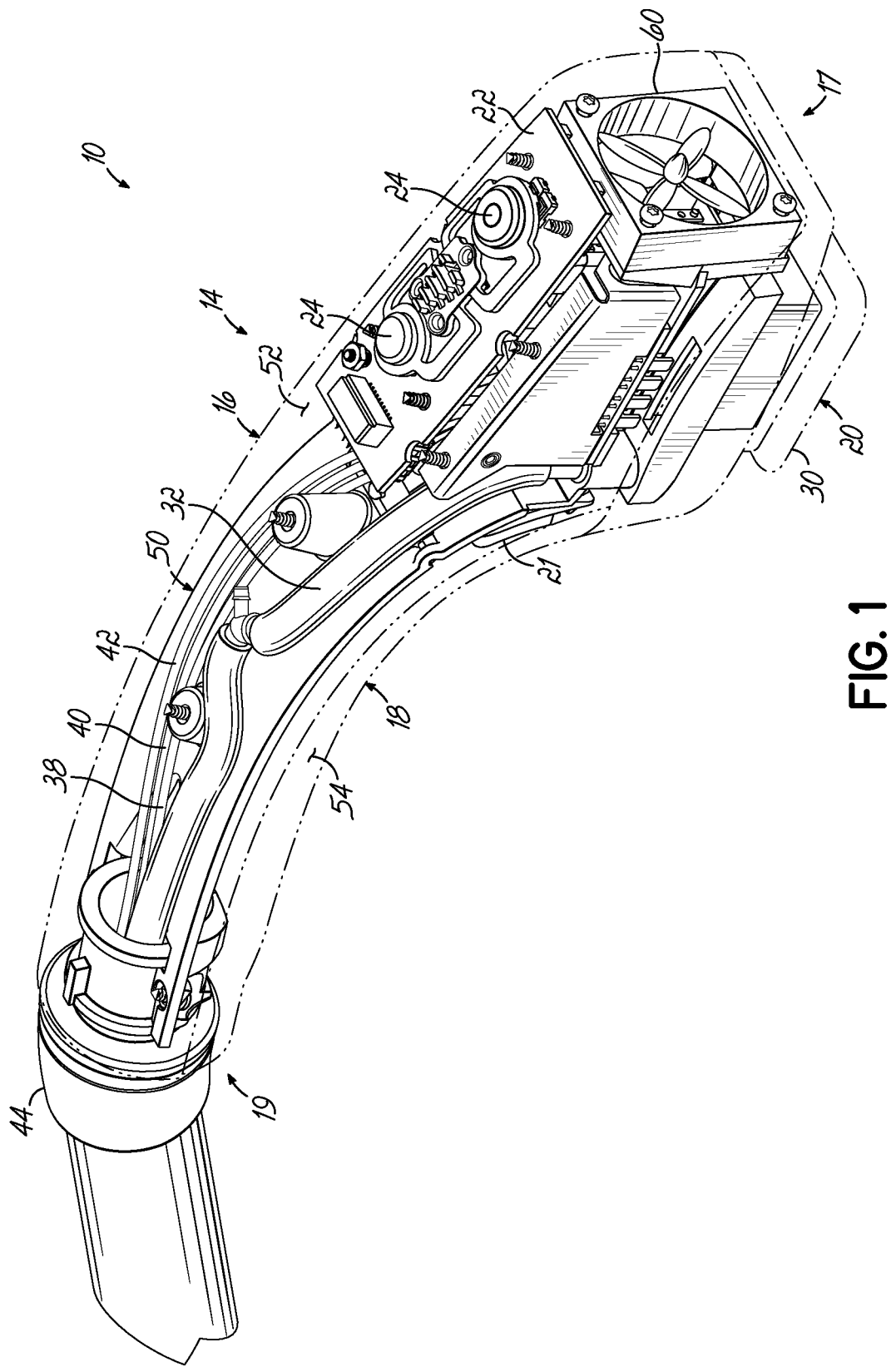
FIG. 1 is a perspective view of a handpiece constructed in accordance with an embodiment of the invention.
Figure 2:
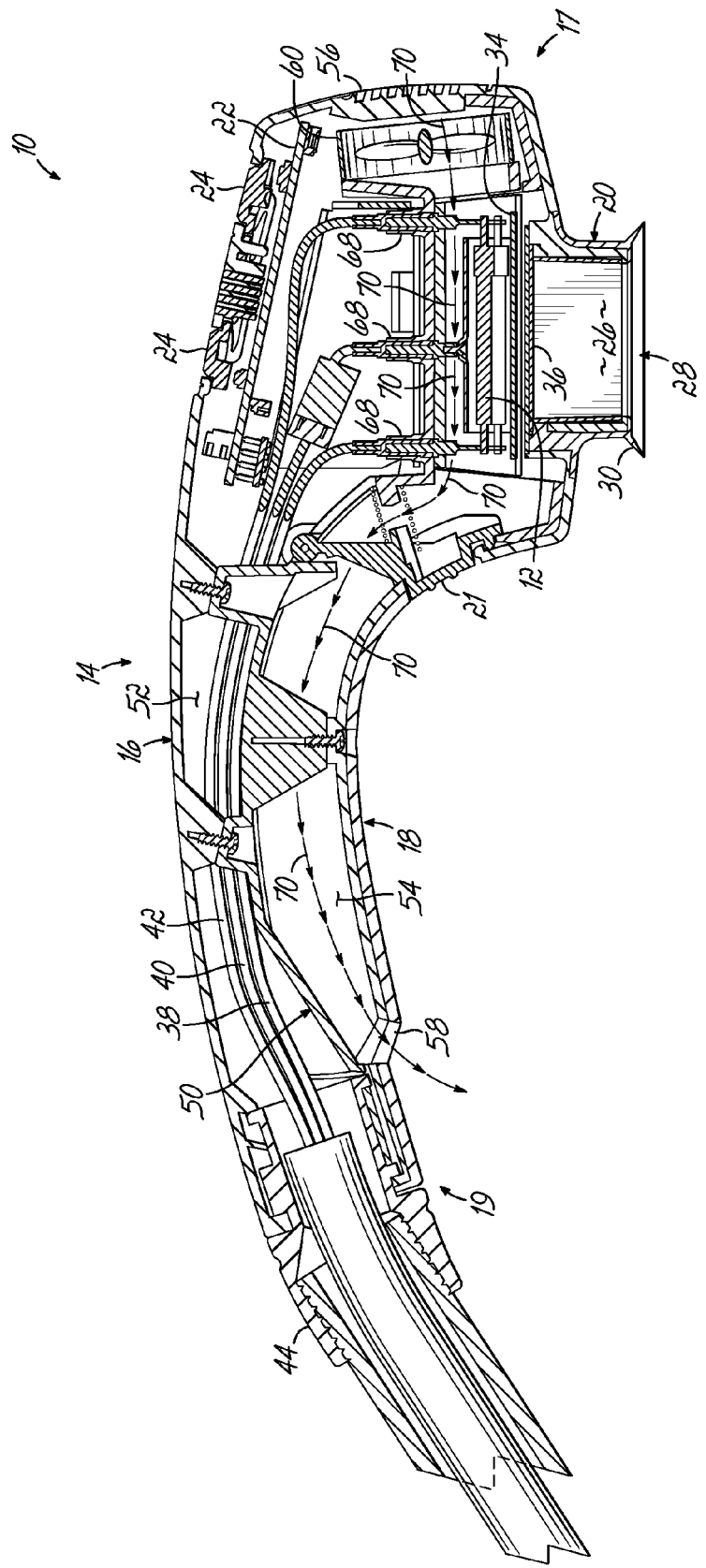
FIG. 2 is a cross-sectional view of the handpiece of FIG. 1.
Figure 3:
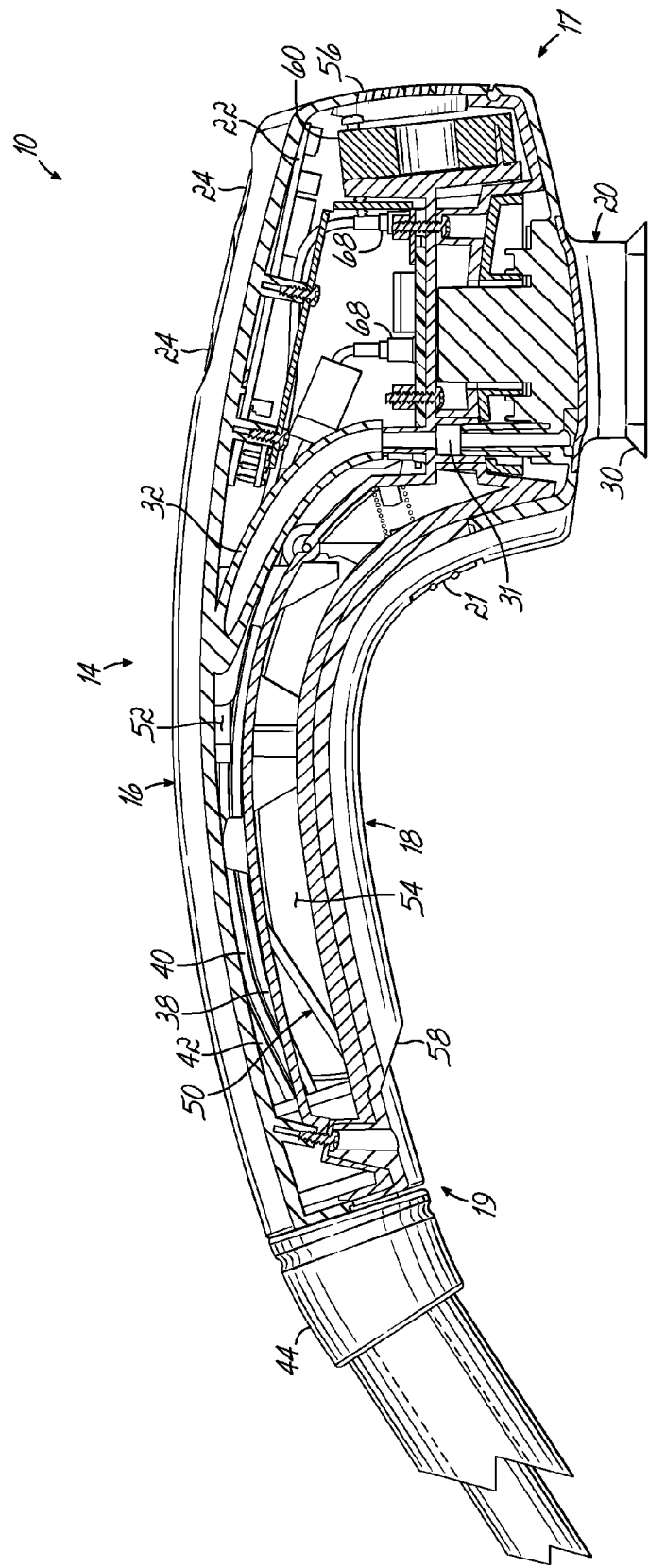
FIG. 3 is another cross-sectional view similar to FIG. 2 but taken along a different plane in FIG. 1.

With reference to FIGS. 1-3, a medical handpiece 10 is provided that generates electromagnetic radiation for use in treating skin tissue and the like for medical and cosmetic purposes. The medical handpiece 10 includes a hand-held housing 14 that is sectioned into an upper housing 16 and a lower housing 18, as well as a removable tip 20 that is attached to the lower housing 18. The upper and lower housings 16, 18 may be joined together by conventional fasteners and threaded posts to form an assembly. When the upper and lower housings 16, 18 are assembled, the housing 14 extends from a first end 17 to a second end 19. When a treatment procedure is performed using the medical handpiece 10, the first end 17 is situated nearest to the patient (i.e., proximal) and the second end is situated farthest from the patient (i.e., distal).

The removable tip 20 may be a consumable item that is patient and/or treatment specific. A push latch 21 may be provided as a release mechanism for use in mechanically attaching the removable tip 20 to the housing 14 and detaching the removable tip 20 from the housing 14.

The medical handpiece 10 includes an electromagnetic radiation (EMR) source 12 that is located at an end of the handpiece 10 proximate to the patient when the medical handpiece 10 is operating to perform a medical procedure. The EMR source 12 generates and emits electromagnetic radiation. In one embodiment, the EMR source 12 may be any type of source understood by a person having ordinary skill in the art as being applicable to generate electromagnetic radiation for use in a medical procedure that treats a skin condition or skin tissue by phototherapy. In a representative embodiment, the electromagnetic radiation source 12 may be a flash lamp or similar light source having one or more bulbs or lamps configured to generate optical radiation comprising broadband light in a pulsed operation mode or in a switched continuous operation mode.

The EMR source 12 is controlled by circuitry mounted on a circuit board 22 disposed inside the housing 14. The circuitry on the circuit board 22 may include an AC-to-DC converter, a driver circuit, a switching circuit, a microprocessor that controls the switching and driving circuits, discrete elements such as resistors, capacitors and inductors, etc. Control switches 24 are accessible from the exterior of the housing 14 and may be connected with the circuit board 22. The control switches 24 may provide a user interface for selecting treatment procedure settings (e.g., intensity of the electromagnetic radiation) for the operation of the EMR source 12 and for activating the EMR source 12 to initiate exposure of the skin surface to electromagnetic radiation during a treatment procedure.

One end of the removable tip 20 includes a suction chamber 26, a chamber opening 28 to the chamber 26, and a flexible skirt 30 that encircles the rim of the chamber opening 28. When the removable tip 20 is placed into contact with the skin surface, the flexible skirt 30 forms a seal with the skin surface. A suction port 31 is coupled with the suction chamber 26 and is supplied with suction (i.e., negative pressure or vacuum) through a vacuum conduit 32 that is coupled with a vacuum pump (not shown). When the flexible skirt 30 contacts the skin surface, the chamber opening 28 is substantially sealed by the contacting relationship because the skin surface occludes the chamber opening 28 and a pressure less than atmospheric pressure can be established in the suction chamber 26.

The electromagnetic radiation from the EMR source 12 is directed though windows 34, 36 disposed between the EMR source 12 and the suction chamber 26 in a propagation path thorough the suction chamber 26 toward the chamber opening 28. Window 34 may be configured to filter the electromagnetic radiation from the EMR source 12 so that only electromagnetic radiation within a defined wavelength band is transmitted. Window 36 may be configured to provide a vacuum seal with the suction chamber 26 in the removable tip 20. The windows 34, 36 define an aperture through which the electromagnetic radiation is emitted from the housing 14 and directed toward the skin surface during a treatment procedure. The EMR source 12 may further include a reflector configured to direct a portion of the electromagnetic radiation toward the windows 34, 36.

A plurality of cables 38, 40, 42, as well as the vacuum conduit 32, may enter the housing 14 through a boot 44 at the rear of the housing 14. The cables 38, 40, 42 may transfer high voltage from an external high voltage power supply to the EMR source 12, as well as transfer communications signals between the circuit board 22 and a control console and low voltage from an external lower voltage power supply to the circuit board 22. In the representative embodiment, the cables 38, 40, 42 are high voltage cables coupled with the EMR source 12; however, the invention is not so limited as one or more of the cables 38, 40, 42 and/or additional cables (not shown) similar to cables 38, 40, 42 may be used for communications signals or to transfer low voltage.

During a treatment, the housing 14 is manipulated to place the removable tip 20 into a contacting relationship with the skin surface. The skirt 30 provides at least a partial seal with the skin surface and the vacuum supplied via the vacuum tube is applied to the surface area of the skin surface peripherally inside the skirt 30. The vacuum applies an unbalanced suction force to this skin surface area that lifts the skin surface through the chamber opening 28 and into the suction chamber 26 inside the tip. The vacuum in the suction chamber 26 may loosen and extract dirt, blackheads, dead cells, and excess oil from the skin pores of the stretched skin. After a time delay and while the vacuum is maintained, the EMR source 12 is then activated using the controls and managed by the circuitry on the circuit board 22. For example, high voltage may be supplied to the EMR source 12 to generate electromagnetic radiation. The electromagnetic radiation may destroy bacteria on the skin surface and may also slough the oils and dead skin cells away. After illumination with the electromagnetic radiation, the connection of the suction chamber 26 to the EMR source 12 is broken and the suction chamber 26 is returned to the atmosphere. The stretched skin relaxes back to its original shape. The process is repeated to treat multiple surface areas. The combination of exposure to vacuum and electromagnetic radiation during the procedure may provide, for example, an effective acne treatment.

A partition or baffle 50 is positioned inside the handpiece 10 and is disposed as a divider in the interior space inside the housing 14 so that the interior space is segmented lengthwise into an upper channel 52 and a lower channel 54. The vacuum conduit 32 and the cables 38, 40, 42 are routed through the upper channel 52 so that the vacuum conduit 32 and the cables 38, 40, 42 are segregated from the lower channel 54. Conversely, the lower channel 54 is free of cables 38, 40, 42 and is instead unobstructed by these types of structures that supply high and low voltage power, as well as communications signals. Window 36 may isolate the suction chamber 26 in the removable tip 20 from the lower channel 54. Electrical couplings 68 extend through the baffle 50 to connect the cables 38, 40, 42 with the EMR source 12.

The upper and lower channels 52, 54 each extend from the first end 17 of the housing 14 to the second end 19 of the housing 14. The upper and lower channels 52, 54 are arranged in parallel to each other, are non-concentric, and do not communicate with each other due to the presence of the baffle 50. The lower channel 54 extends from an opening 56 defining an inlet at one end of the housing 14 to an opening 58 defining an outlet at an opposite end of the housing 14. The inlet opening 56 may include louvers that section the inlet opening 56 into plural openings. The outlet opening 58 may be any closed geometrical shape (e.g., rectangular or circular) and may be free of louvers and the like. Neither the inlet opening 56 nor the outlet opening 58 is coupled with the upper channel 52.

A portion of the electrical energy supplied to the EMR source 12 is used to generate electromagnetic radiation for the treatment procedure. Another portion of the electrical energy is dissipated by the EMR source 12 to generate heat energy. When energized and operating to generate electromagnetic radiation, the EMR source 12 therefore requires cooling in order to maintain the temperature of the EMR source 12 at or below an operating temperature threshold often recommended by the manufacturer. Otherwise, the EMR source 12 may be prone to premature failure due to overheating. Other structures inside the housing 14 may also represent heat-generating sources in addition to the EMR source 12.

An air-moving device 60, such as a blower or fan, is coupled with the lower channel 54 and is configured to generate a forced flow of cooling air for the EMR source 12. The air-moving device 60 may be controlled by the circuit board 22 and may receive low voltage power when energized to operate. The forced flow of cooling air is generally indicated by the single-headed arrows 70.

In the representative embodiment, the air-moving device 60 is positioned in the lower channel 54 between the inlet opening 56 and the EMR source 12. The air-moving device 60 intakes cooling air at ambient temperature through the inlet opening 56, which is located proximate to the patient during a treatment procedure. The cooling air in the forced flow is heated by passage within the lower channel 54 in proximity to the EMR source 12. Specifically, the cooling air receives heat transferred from the EMR source 12, which cools the EMR source 12. The cooling air may be heated significantly above ambient temperature, for example to about 120° C. The heated cooling air with the elevated temperature is exhausted from the lower channel 54 through the outlet opening 58 at the rear of the medical handpiece 10 and in a direction away from the patient and away from the tissue that is being treated with the electromagnetic radiation. By discharging the heated cooling air at the end 19 that is more remote from the patient than end 17, patient comfort is enhanced relative to handpiece designs in which the heated cooling air is discharged toward the patient. The flow of cooling air through the lower channel 54 is indicated diagrammatically in FIG. 2 by the string of single headed arrows 70.

In contrast to the upper channel 52, the lower channel 54 is free of electrical cables and is instead unobstructed by these types of structures for transferring high voltage power, low voltage power, and communications signals from external sources into the medical handpiece 10. The flow rate of the cooling air in the lower channel 54 is proportional to the fluid velocity and also to the cross-sectional area intersected by the flow. The flow rate of the cooling air through the lower channel 54 is enhanced and optimized by the absence of obstructions to air flow, which effectively increases the cross-sectional area intersected by the flow of cooling air. The upper channel 52 and the cables 38, 40, 42 therein are isolated by the baffle 50 from the forced flow of cooling air through the lower channel 54.

The air-moving device 60 and the EMR source 12 are each positioned closer to the inlet opening 56 than to the outlet opening 58. The aperture provided by windows 34, 36 and through which the electromagnetic radiation is emitted from the housing 14 is likewise positioned closer to the inlet opening 56 than to the outlet opening 58. The length of the lower channel 54 permits the heated cooling air to cool during transit from the inlet opening 56 to the outlet opening 58. As a result of the reduction in temperature, the individual holding the handpiece 10 during the treatment procedure is exposed to a forced air flow having a reduced temperature. For example, the heated cooling air may cool from 120° C. at the location of the EMR source 12 to 70° C. or 80° C. when exhausted from the outlet opening 58 of the handpiece 10.

References herein to terms such as "vertical", "horizontal", etc. are made by way of example, and not by way of limitation, to establish a three-dimensional frame of reference. Terms, such as "upper", "lower", "on", "above", "below", "side" (as in "sidewall"), "higher", "lower", "over", "beneath" and "under", are defined with respect to the horizontal plane. It is understood that various other frames of reference may be employed without departing from the spirit and scope of the invention as a person of ordinary skill will appreciate that the defined frame of reference is relative as opposed to absolute.

While the invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept. The scope of the invention itself should only be defined by the appended claims.

What is claimed is:

1. An apparatus for treating tissue with electromagnetic radiation, the apparatus comprising:
    a handpiece including a suction port that provides a negative pressure, a housing, and a baffle that divides an interior space of the housing into a first channel and a second channel isolated from the first channel by the baffle, the housing including a first opening and a second opening coupled in fluid communication with the first opening by the first channel;
    a heat-generating element disposed at least partially in the first channel; and
    an air-moving device coupled with the first channel, the air-moving device configured to generate a forced flow of air entering at the first opening and exhausted at the second opening,
    wherein the isolation of the first channel from the second channel keeps the forced flow of air from moving through the second channel, the housing has a first end adjacent the first opening and a second end adjacent the second opening, the baffle extends from the first end to the second end to divide the handpiece along an entire length of the housing into the first and second channels, the first and second channels are non-concentric, the second channel receives an electrical cable coupled with the heat-generating element and that extends in the second channel from the heat-generating element to a location external to the handpiece, the first channel is free from flow obstructions other than the heat-generating element and the air-moving device to optimize the forced flow of air used to cool the heat-generating element, and the air-moving device is positioned between the first opening and the heat-generating element.

2. The apparatus of claim 1 wherein the heat-generating element is an electromagnetic radiation source.

3. The apparatus of claim 1 wherein the air-moving device is a fan.

4. The apparatus of claim 1 wherein the heat-generating element is an electromagnetic radiation source configured to generate electromagnetic radiation and heat energy while generating the electromagnetic radiation, and the housing has an opening through which the electromagnetic radiation can be transmitted towards a skin surface.

5. The apparatus of claim 4 wherein the opening is sealed by a window configured to transmit the electromagnetic radiation from the housing, and the window is positioned closer to the first opening than to the second opening.

6. The apparatus of claim 1 wherein the first channel and the second channel have a parallel arrangement.

7. The apparatus of claim 1 further comprising:
    an electrical coupling extending through the baffle for coupling the electrical cable with the heat-generating element.

8. The apparatus of claim 1, wherein each of the air-moving device and the heat-generating element is positioned closer to the first opening than to the second opening such that air flowing through the first channel and heated to a first temperature by the heat-generating element cools to a second temperature lower than the first temperature before discharge at the second opening, thereby reducing exposure of a user of the handpiece to air flow at elevated temperatures, and the heat-generating element is an electromagnetic radiation source delivering heat energy through a window located closer to the first opening than the second opening, thereby separating exhausted heated air at the second opening from a treatment location adjacent the window by a majority of the housing, to avoid excessive heat generation adjacent the window.

9. The apparatus of claim 1 further comprising:
    a removable tip that is attached to the housing, the removable tip including a suction chamber that is coupled to the suction port of the housing and that is supplied with the negative pressure from the suction port.

10. The apparatus of claim 9 wherein the removable tip further includes a window through which the electromagnetic radiation is directed into the suction chamber.

11. The apparatus of claim 9 further comprising:
    a vacuum conduit that couples the suction port to a vacuum pump and that is routed through the second channel.

12. A method for treating tissue with electromagnetic radiation, the method comprising:
    applying a negative pressure to a surface area of the tissue using a handpiece;
    directing the electromagnetic radiation out of the handpiece to treat the tissue;
    causing a forced flow of air to enter through a first opening into a first channel extending through the handpiece;
    directing the forced flow of air within the first channel to transfer heat from a heat-generating element to the forced flow of air;

after the heat transfer, exhausting the forced flow of air from the first channel through a second opening; and powering the heat-generating element with electrical power transferred using a cable positioned in a second channel inside the handpiece that is isolated from the first channel, wherein the isolation of the first channel from the second channel is provided by a baffle that keeps the forced flow of air from moving through the second channel, the housing has a first end adjacent the first opening and a second end adjacent the second opening, the baffle extends from the first end to the second end to divide the handpiece along an entire length of the housing into the first and second channels, the first and second channels are non-concentric, the second channel receives an electrical cable coupled with the heat-generating element and that extends in the second channel from the heat-generating element to a first location external to the handpiece, the first channel is free from flow obstructions other than the heat-generating element and an air-moving device to optimize the forced flow of air used to cool the heat-generating element, and the air-moving device is positioned between the first opening and the heat-generating element.

13. The method of claim 12 wherein the heat-generating element is an electromagnetic radiation source, and further comprising:

generating the electromagnetic radiation with the electromagnetic radiation source.

14. The method of claim 13 wherein the electromagnetic radiation is directed out of the handpiece at a second location proximate to the tissue, the first opening is proximal to the tissue receiving the electromagnetic radiation, and the second opening is distal from the tissue.

15. The method of claim 12 wherein the forced flow of air is caused by operation of a fan.

* * * * *